(12) United States Patent
Sulejmani (10) Patent No.: US 11,234,375 B2
(45) Date of Patent: Feb. 1, 2022

(54) METHOD FOR INCREASING THE FLORAL YIELD OF A FLOWERING PLANT

(71) Applicant: Sulejmani Holdings, LLC, Livonia, MI (US)

(72) Inventor: Memet Sulejmani, Livonia, MI (US)

(73) Assignee: Sulejmani Holdings, LLC, Warren, MI (US)

( * ) Notice: Subject to any disclaimer, the term of this patent is extended or adjusted under 35 U.S.C. 154(b) by 105 days.

(21) Appl. No.: 16/437,577

(22) Filed: Jun. 11, 2019

(65) Prior Publication Data

US 2020/0390039 A1 Dec. 17, 2020

(51) Int. Cl.
| | |
|---|---|
| *A01G 7/04* | (2006.01) |
| *F21V 21/088* | (2006.01) |
| *A01G 22/60* | (2018.01) |
| *A01H 3/02* | (2006.01) |
| *A01H 6/28* | (2018.01) |

(52) U.S. Cl.
CPC ............. *A01G 7/045* (2013.01); *A01G 22/60* (2018.02); *A01H 3/02* (2013.01); *A01H 6/28* (2018.05)

(58) Field of Classification Search
CPC .......... A01G 7/045; A01G 22/60; A01H 3/02; A01H 6/28
USPC ......................................................... 47/58.1
See application file for complete search history.

(56) References Cited

U.S. PATENT DOCUMENTS

| | | | |
|---|---|---|---|
| 5,571,125 A | 11/1996 | Chadwick | |
| 7,401,936 B1 | 7/2008 | Fan | |
| 8,796,949 B2 | 8/2014 | Awamoto et al. | |
| 2007/0133191 A1 | 6/2007 | Ma | |
| 2010/0287830 A1 | 11/2010 | Chen et al. | |
| 2013/0139437 A1 | 6/2013 | Maxik et al. | |
| 2015/0181811 A1 | 7/2015 | Krijn et al. | |
| 2016/0184237 A1* | 6/2016 | Lowe et al. | A61K 31/05 |
| 2017/0290274 A1 | 10/2017 | Sulejmani | |

FOREIGN PATENT DOCUMENTS

| | | | |
|---|---|---|---|
| JP | 2002272271 | * | 9/2002 |
| JP | 2005328702 | * | 12/2005 |
| JP | 2005328702 A | | 12/2005 |
| JP | 2007267645 A | | 10/2007 |
| WO | WO 2013/131024 | * | 9/2013 |
| WO | WO2013131024 | * | 9/2013 |
| WO | WO2013131024 A1 | | 9/2013 |
| WO | WO2014013400 A2 | | 1/2014 |

OTHER PUBLICATIONS https://www.ilovegrowingmarijuana.com/led-marijuana-grow-lights/.*
https://indoorgardening.com/best-clip-on-grow-lights-for-indoor-plants/ Mar. 2019.*
The Cannabis Encyclopedia Jorge Cervantes. Chapter 17 . . . 2015.*
"3 Types of Marijuana Grow Lights. Which will yield the biggest Crop?", https://www.how-to-marijuana.com/marijuana-grow-lights.html, accessed Jun. 10, 2019.
Paul Deram, "Supplemental Lighting Orientation and Red-to-blue Ratio of Light-emitting Diodes for Greenhouse Tomato Production", HortScience, 2014, p. 1-5, 49(4):488-452.

* cited by examiner

*Primary Examiner* — Annette H Para
(74) *Attorney, Agent, or Firm* — Quinn IP Law (57) ABSTRACT

A method for increasing floral yield of a flowering plant includes positioning the plant between side lights at the onset of a flowering stage of the plant, such that the plant is flanked by the side lights. The method also includes irradiating lateral sides of the flowering plant along the total height via the side lights with light in a predetermined red spectrum range for a duration of the flowering stage, such that at least 80 percent of the light has a wavelength of between 580 nm and 780 nm. The plant may be positioned between first and second sets of equally-spaced elongated side lights on respective first and second lateral sides of the plant. Supplemental lighting devices may be attached to the plant, with an interior of the plant irradiated with the red spectrum light for the duration of the flowering stage using the lighting devices.

18 Claims, 4 Drawing Sheets

METHOD FOR INCREASING THE FLORAL YIELD OF A FLOWERING PLANT

TECHNICAL FIELD

The present disclosure relates to a method for increasing the floral yield of a flowering plant.

BACKGROUND

Flowering plants grow from a seed into a fully mature plant through a progressive series of lifecycle stages. Depending on the plant variety, such lifestyle stages typically include germination, seedling, vegetative growth, bloom/flowering, and harvest stages. Common examples of flowering plants are floral plants such as orchids and lilies, with tomato plants being a fruit-producing variety of flowering plant. Cannabis is another example of a flowering plant, one whose consumable floral blooms/buds have certain medicinal properties. Such plants can progress rapidly from seed to harvest in as little as 4-10 months.

As disclosed in U.S. Pat. No. 6,630,507 to Hampson et al., as originally assigned to the United States of America as Represented by The Department of Health and Human Services, cannabinoids found in cannabis plants have certain antioxidant properties that have proven to be useful in the treatment of a variety of inflammatory, autoimmune, and other diseases. Medically-prescribed cannabis/marijuana is therefore growing as a government-regulated alternative means for relieving nausea, pain, and other symptoms of debilitating diseases. Some government entities also begun to permit the limited sale and use of controlled amounts of marijuana for recreational use. As a result, a nascent but growing industry of cannabis cultivation devices and methodologies has emerged.

The flowering stage of growth is of particular importance to the cultivation of cannabis and other flowering plants having a similar lifecycle. During the flowering stage, male plants produce pollen for fertilization of the blooms of the female plants. The pollinated flowers or buds in turn produce the seeds that are necessary for germinating another plant, thereby ensuring longevity of a particular crop of plants. With respect to cannabis in particular, the flowers of non-pollinated female plants are carefully harvested, dried, and cured at the harvesting stage. The buds are then processed for human consumption. Therefore, a substantial bud yield during the flowering stage of a plant's lifecycle is desirable. However, existing methods for the cultivation of cannabis and other flowering plants may be less than optimal in terms of maximizing such a yield.

For instance, conventional methods of cultivation include the use of broad-spectrum lighting panels, which is typically achieved via the use of bright overhead "grow light" panels, natural sunlight, or multi-spectral bands of light such as the blue-red spectrum. Compact fluorescent lamps, metal halide, high-pressure sodium grow lights, and light-emitting diode panels are examples of conventional lighting panels. Such lighting panels are typically positioned a few inches to a few feet above the canopy of the plant, and are used throughout the entirety of the vegetative and flowering stages of the plant's life cycle. However, such panels may be less than optimal in terms of floral yield, i.e., the amount or volume of floral buds or blooms produced by the flowering plant.

SUMMARY

A method is disclosed herein for increasing the floral yield of a flowering plant. In an example embodiment, the method includes irradiating the lateral sides of the flowering plant with red spectrum light for the duration of the flowering stage of the plant's lifecycle. Side lighting of the plant with red spectrum light may be optionally supplemented via targeted placement of additional lighting devices within the plant's canopy, e.g., clamped directly to a stalk of the plant, staked to the ground, and/or hung from the plant's individual branches. The method may be used in conjunction with full-spectrum overhead lighting in some embodiments.

Low relative power consumption is a potential problem when using full-spectrum lighting, such as combined blue/red LED overhead grow panels. While low power consumption makes LED lighting panel technologies an energy-efficient lighting option, it is recognized herein that low power consumption can potentially result in poor penetration of light through the canopy of the flowering plant. Plant growth occurs rapidly during the flowering stage of the plant's lifecycle during which, depending on the plant variety, the canopy can quickly reach a height above soil level of at least 2-4 feet. As a result of such limitations, conventional growing processes tend to require extensive pruning of the lower portions of the canopy. This in turn can stress the plant and possibly stunt the growth and yield of the plant's floral blooms or buds. The present method is therefore intended to address such cultivation problems of cannabis and other flowering plants having a similar lifecycle.

In a particular embodiment, the method includes positioning the flowering plant between side lights at an onset of a flowering stage of the flowering plant, such that the flowering plant is flanked by the side lights, and irradiating the flowering plant along the total height, via the side lights, with light in a predetermined red spectrum range of the electromagnetic spectrum for a duration of the flowering stage. At least 80 percent of the light has a wavelength of between 580 nm and 780 nm.

Positioning the flowering plant between the side lights may include positioning the flowering plant between first and second sets of equally-spaced side lights on respective first and second sides of the flowering plant.

The method may include attaching one or more supplemental lighting devices to the flowering plant within an interior or under-canopy region of the flowering plant, and then irradiating the interior or under-canopy region with the light in the predetermined red spectrum range for the duration of the flowering stage using the one or more supplemental lighting devices.

Attaching the one or more supplemental lighting devices to the flowering plant may include clamping at least one an annular clamshell-shaped lighting device directly to a stalk of the flowering plant. Alternatively, the method may include supporting the at least one an annular clamshell-shaped lighting device using a plurality of legs, each respective one of which extends between and at least partially into the annular clamshell-shaped lighting device and the soil.

The annular clamshell-shaped lighting device may be equipped with spring-loaded clamps biased by a spring force. Clamping the annular clamshell-shaped lighting device directly to the stalk of the flowering plant may occur solely via the spring force of each of the spring-loaded clamps, such that the stalk is fully circumscribed or surrounded by the annular clamshell-shaped lighting device.

The annular clamshell-shaped lighting device may also include first and second annular clamshell-shaped lighting devices arranged back-to-back, with the method including directing the light from the device upward and downward into the interior or under-canopy region of the flowering plant.

At least 95 percent of the light may have a wavelength on the predetermined red spectrum range and a color of between 1500 and 2700 degrees Kelvin. The predetermined red spectrum range may be between 585 nm to 740 nm, e.g., 600 nm to 700 nm.

The flowering plant may be a cannabis plant in some embodiments.

The method for increasing the floral yield of a flowering plant in another embodiment includes positioning the flowering plant between parallel first and second sets of equally-spaced elongated side lights at an onset of a flowering stage of the flowering plant, such that the flowering plant is flanked by the parallel side lights, and such that a first respective one of each of the first and second sets of equally-spaced elongated side lights is positioned proximate a top of the flowering plant, a second respective one of each of the first and second sets of equally-spaced elongated side lights is positioned proximate a bottom of the flowering plant, and at least a third respective one of each of the first and second sets of equally-spaced elongated side lights are positioned proximate a middle of the flowering plant.

Such an embodiment also includes attaching at least one supplemental lighting device to an interior or under-canopy region of the flowering plant, and then irradiating the lateral sides of the flowering plant along the total height via the first and second sets of equally-spaced elongated side lights, and irradiating the interior of the flowering plant via the at least one lighting device, with light in a predetermined red spectrum range of the electromagnetic spectrum for a duration of the flowering stage. At least 80 percent of the light has a wavelength in the predetermined range of 580 nm to 780 nm.

The above features and advantages and other features and advantages of the present disclosure are readily apparent from the following detailed description of the best modes for carrying out the disclosure when taken in connection with the accompanying drawings.

The present disclosure is susceptible to modifications and alternative forms, with representative embodiments shown by way of example in the drawings and described in detail below. Inventive aspects of this disclosure are not limited to the disclosed embodiments. Rather, the present disclosure is intended to cover modifications, equivalents, combinations, and alternatives falling within the scope of the disclosure as defined by the appended claims.

DETAILED DESCRIPTION

All numerical values of parameters of quantities or conditions in this specification, including the appended claims, are to be understood as being modified in all instances by the term "about", whether or not "about" actually appears before the numerical value. The term "about" as used herein indicates that the stated numerical value allows for slight imprecision with respect to exactness in the stated value or range, i.e., reasonably close or nearly. If the imprecision provided by the term "about" is not otherwise understood in the art with this ordinary meaning, then "about" as used herein indicates at least variations that may arise from ordinary methods of measuring and using such parameters, for instance ±5 percent of the stated value or range. In addition, disclosure of ranges includes disclosure of all values and further divided ranges within the entire range.

Figure 1:
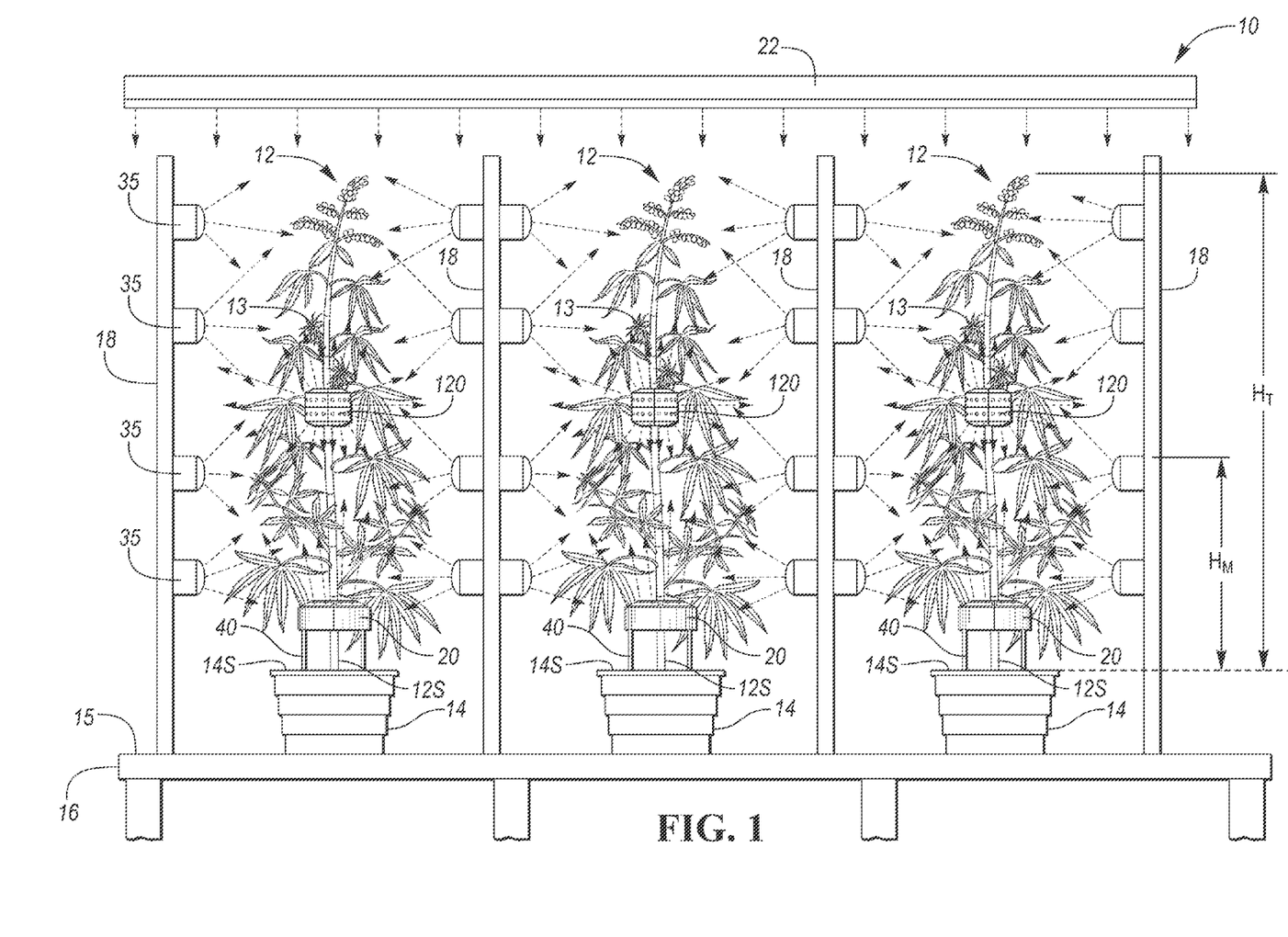
FIG. 1 is a schematic perspective view illustration of an exemplary growing operation in which multiple rows of flowering plants are irradiated with red spectrum light from LED-based lighting devices configured, positioned, and controlled in accordance with the present methodology.

Referring to the drawings, wherein like reference numbers refer to the same or similar components throughout the several views, an example growing operation 10 of flowering plants 12 is shown schematically in FIG. 1. The present teachings may be applied during the flowering stage of one or more such flowering plants 12. The method of performing the growing operation 10 as described herein may be advantageous when cultivating a variety of plant having such a flowering stage as part of its lifecycle. For example, the flowering plants 12 may be a variety of cannabis plant, such as *Cannabis sativa, Cannabis indica*, or a hybrid variant thereof. Alternatively, the flowering plants 12 may be a common floral plant such as an iris or lily plant, or the flowering plants 12 may be a flowering fruit-bearing plant such as a tomato plant. A cannabis plant as shown generically in FIGS. 1 and 5 will be described hereinafter for illustrative consistency without limiting applications to such a plant.

The flowering plants 12 may be rooted in soil contained within a pot 14, the size and shape of which may vary from the simplified example depiction of FIG. 1. Each respective one of the flowering plants 12 has buds or floral blooms 13 of various sizes during the above-noted flowering stage. Each flowering plant 12 has a total height ($H_T$) as measured from a surface 14S of soil within the pot 14 to the uppermost reaches of the canopy of the flowering plant 12. Additionally, each flowering plant 12 has a middle height ($H_M$), which as defined herein refers to approximately half of the total height ($H_T$), e.g., within 40 to 60 percent of the total height ($H_T$).

As disclosed herein and described below with reference to FIG. 6, a method 100 may be used to increase the floral yield of the flowering plants 12 shown in FIG. 1 relative to existing plant cultivation and grow light-augmented processes. The method 100 includes irradiating the lateral sides and possibly interior surfaces of the flowering plant 12 with predominantly red spectrum light emitted from specially-positioned and configured lighting devices. The use of the described red spectrum light alone, and not as part of a broader spectrum of incident light, occurs specifically during the flowering stage of the flowering plant 12, with the term "red spectrum" having the meaning ascribed herein. That is, the term "predominantly red" and "red spectrum" refers to light falling in a defined spectrum in which at least 80% of the emitted light falls within the predetermined range of 580 nm to 780 nm, and therefore always includes at least the red spectrum of visible light. The light may have a color of between 1500 and 2700 degrees Kelvin. Limited amounts of yellow and/or orange light may be included in the spectrum in some embodiments.

The LED-based lighting devices contemplated herein include a plurality of side lights 35 configured to irradiate the lateral sides of the flowering plants 12. That is, the side lights 35 are stacked adjacent to the flowering plants 12 such that the flowering plants 12 are flanked by rows of the side lights 35. For instance, multiple side lights 35 may be mounted on vertical racks 18 supported by a surface 15 of a platform 16. Although omitted for clarity, the platform 16 may be mounted to wheels to facilitate movement of the flowering plants 12 throughout a growing facility.

In a possible embodiment, each of the side lights 35 may be configured as an elongated lighting device, e.g., T8-size low-wattage bulb powered by a separate power supply (not shown) or by the grid. The side lights 35 may be arranged parallel to each other and/or equally spaced in the vertical direction as shown, and are arranged to form multiple light columns C1, C2, C3, and C4 extending along the total height ($H_T$) of the flowering plants 12, e.g., four equally-spaced parallel side lights 35 as shown. In the example of FIG. 1 in which three flowering plants 12 are depicted, only the three outermost flowering plants 12 in extended rows of the flowering plants 12 are visible from the perspective of FIG. 1.

Each row of the flowering plants 12 is flanked by a respective pair of the vertical racks 18, with each vertical rack 18 outfitted with the side lights 35 as noted above, i.e., with light columns C1 and C2 flanking one of the flowering plants 12, light columns C2 and C3 flanking another flowering plant 12, light columns C4 and C4 flanking another flowering plant 12, and so forth. Unlike approaches that utilize broad-spectrum light, or even targeted spectrum light arranged as "under-canopy" lighting, e.g., by arranging lighting devices on the ground and orienting the light upward into the lowest reaches of the canopy, the present approach illuminates the entirety of the total height ($H_T$) of the flowering plants 12 from the sides with the specified red spectrum light, doing so commencing at the onset of the flowering stage and discontinuing such targeted red-spectrum lighting upon completion of the flowering stage.

The side lights 35 collectively emit light, as indicated by the various arrows in FIG. 1, in a predetermined range of the electromagnetic spectrum, i.e., predominantly in the range of 580 nm to 780 nm. Unlike existing overhead grow light panels and other lighting technologies of the types noted above, an example of which is shown at 22 and which typically irradiates the flowering plant 12 from overhead with blue-red light or the entire spectrum of light during multiple stages of the lifecycle of the plant 12, the predetermined range of the electromagnetic spectrum as used herein includes red spectrum light of which at least 80% of the energy or power output of the side lights 35 has a red spectrum wavelength range of between about 560 nm and about 740 nm, i.e., the yellow-orange-red spectrum.

In another embodiment, the predetermined range of the electromagnetic spectrum is between about 585 nm and about 740 nm, i.e., the orange-red spectrum, or between about 625 nm and about 740 nm, about 625 nm and about 700 nm, or about 600 nm and about 700 nm, i.e., the red spectrum. The latter range may be used exclusively in a possible approach, as it is recognized herein that 600 nm to 700 nm coincides with a high level of absorbance of the light energy by Chlorophyll a and b. Embodiments may be envisioned that also provide the light having wavelengths that fall within other parts of the electromagnetic spectrum, provided that at least 80% of the emitted light, i.e., substantially all of the emitted light, falls within the disclosed ranges and is thus substantially red light.

As part of the present approach, the red spectrum light emanating from the side lights 35 of FIG. 1 may be optionally supplemented by additional discrete supplemental lighting devices, each of which may irradiate the interior/under-canopy regions of the flowering plant 12 with red spectrum light. Such areas may be difficult to penetrate using the light from the side lights 35. For instance, a full-spectrum lighting panel 22 may be arranged overhead to illuminate the flowering plants 12 from above with the full electromagnetic spectrum, or with light from multiple portions thereof, e.g., blue-red. Additionally, a clamp-on supplemental lighting device 20 (also see FIGS. 2 and 3) may be positioned with respect to the flowering plants 12 at particularly heavy areas of the canopy, such as but not limited to areas at or below the level of the middle height ($H_M$).

In an embodiment, the supplemental lighting device 20 may be clamped directly to a stalk 12S at the interior of the flowering plant 12, such that the lighting device 20 fully circumscribes the stalk 12S. Such an approach may be used when the supplemental lighting device 20 is relatively light and/or the stalk 12S is relatively thick, and thus is able to support the weight of the supplemental lighting device 20 without adversely affecting the flowering plant 12. Optional legs 40 may be used to help offload the weight of the supplemental lighting device 20, as explained below with reference to FIG. 3. An alternative dual clamp-on lighting device 120 is also shown in FIG. 1 and described below with reference to FIG. 4.

Figure 2:
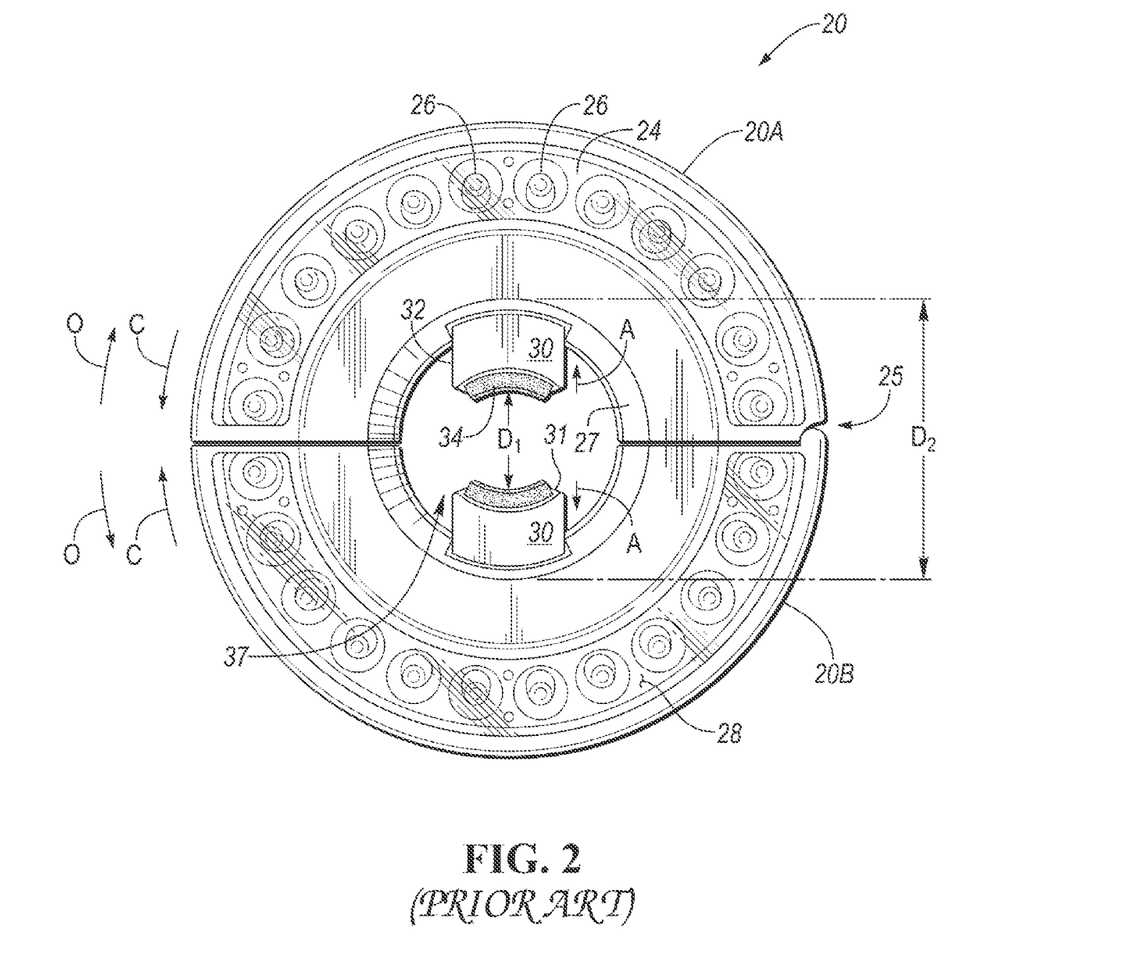
FIG. 2 is a schematic plan view illustration of a prior art spring-loaded LED-based lighting device optionally usable as part of the growing operation of FIG. 1.

Referring to prior art FIG. 2, the clamp-on supplemental lighting device 20 may be configured as an annular clamshell design having a plurality of red LEDs 26 as shown, with the supplemental lighting device 20 in such an embodiment being clamped directly to the stalk 12S of the flowering plant 12. Rather than pruning the floral blooms 13 of FIG. 1 in the lower areas or other heavily canopied areas of the flowering plant 12 in the conventional manner, which can stress the flowering plant 12 and adversely affect its floral yield, the supplemental lighting devices 20 are instead used as needed, where needed, and only for a targeted time and lifecycle stage.

The supplemental lighting device 20 is shown in FIG. 2 according to a possible embodiment as an annular clamshell. Such a design may include respective first and second arcuate halves 20A and 20B joined together via a hinge 25 to form an annular or ring-shaped design. The first and second arcuate halves 20A and 20B may be respectively moved in the direction of arrows C into a closed position as shown in FIG. 2, or in the direction of arrows O to an opened position to enable the stalk 12S to be inserted into the opening 37. A latch release button (not shown) may be located on the underside of the supplemental lighting device 20, biased by a latch spring, and pressed to release a latch on the first arcuate half 20A. Such an embodiment is disclosed in U.S. patent application Ser. No. 15/511,527 which was filed on Mar. 15, 2017, which issued on Oct. 18, 2019 as U.S. Pat. No. 10,433,492B2, and which is hereby incorporated by reference in its entirety.

Each of the first and second arcuate halves 20A and 20B may include an arcuate lighting array 24 having a plurality of red LEDs 26, with the term "arcuate" indicating that the LEDs 26 are arranged in an arc shape as shown. The LEDs 26, as with the side lights 35 of FIG. 1, provide light in the predetermined red spectrum range of the electromagnetic spectrum, such that at least 80 percent of the light or at least 95 percent of the light from each supplemental lighting device 20 is in the predetermined range of 580 nm to 780 nm. For example, each arcuate lighting array 24 may have twelve red LEDs 26 arranged as shown. While shown as transparent for illustrative clarity, an arcuate diffuser lens 28 may be positioned adjacent to the LEDs 26 of each arcuate lighting array 24 to further diffuse the emitted light. Although omitted for simplicity, the reverse side of the lighting device 20, i.e., the side facing the pot 14 in FIG. 1, may include a plurality of battery compartments that house batteries driving a corresponding arcuate lighting array 24.

The lighting device 20 may include a pair of spring-loaded clamps 30, e.g., arcuate or C-shaped clamps as shown, each biased by a spring force, e.g., a return force provided by an internal spring (not shown). Each spring-loaded clamp 30 may include a soft pad 34 disposed on a distal end 31 of a radial body 32. Pressure on the distal end 31 moves a given clamp 30 toward the annular inner wall 27 as indicated by arrows A. The lighting device 20 may be clamped directly to the stalk 12S of the flowering plant 12 shown in FIG. 1, e.g., by positioning the stalk 12S within an inner diameter $D_1$ between the pads 34 within the center opening 37, with the center opening 37 having a diameter $D_2$ that is about twice as large as the diameter $D_1$. The lighting device 20 is thereafter secured to the stalk 12S, e.g., solely via the spring force provided by clamps 30, or using optional legs 40 of FIGS. 1 and 3 to help support the weight of the lighting device 20.

Figure 3:
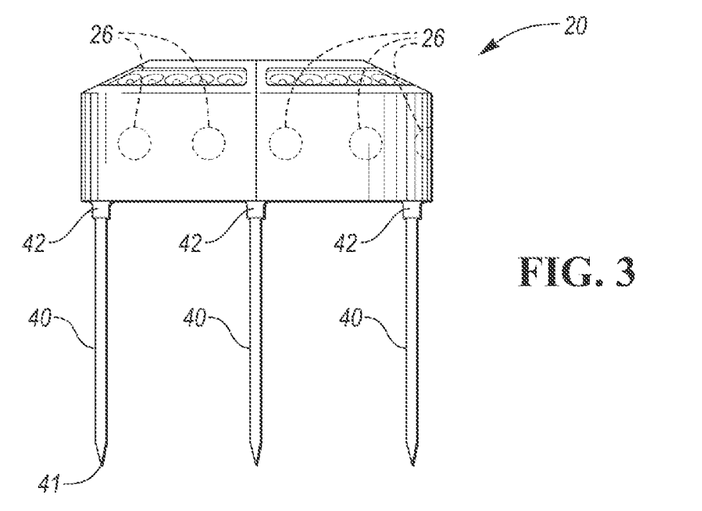
FIG. 3 is a schematic perspective view illustration of the spring-loaded LED-based lighting device of FIG. 2 with optional weight-bearing legs.

Referring briefly to FIG. 3, the supplemental lighting device 20 of FIG. 2, which may be configured with multiple LEDs 26 (shown in phantom) arranged on the sides of the supplemental lighting device 20 to radially project light in the targeted spectrum, may be optionally equipped with optional weight-bearing legs 40, e.g., three such legs 40 as shown. Distal ends 41 of the legs 40, which may be equally-spaced from each other, are shaped to easily penetrate partially into the soil that is contained within the pots 14 shown in FIG. 1. For this purpose, the lighting device 20 may include recesses 42, e.g., openings or receptacles attached to or integrally molded with the supplemental lighting device 20. Such recesses 42 may be configured to receive therein a respective one of the legs 40, for instance in a press fit/interference fit manner, such that the legs 40 penetrate at least partially into the supplemental lighting device 20. When the legs 40 are inserted into the soil, the weight of the supplemental lighting device 20 is effectively offloaded from the stalk 12S and born by the soil. The legs 40 may be available in different lengths to enable placement of the lighting device 20 at different heights within the canopy of the flowering plant 12.

Figure 4:
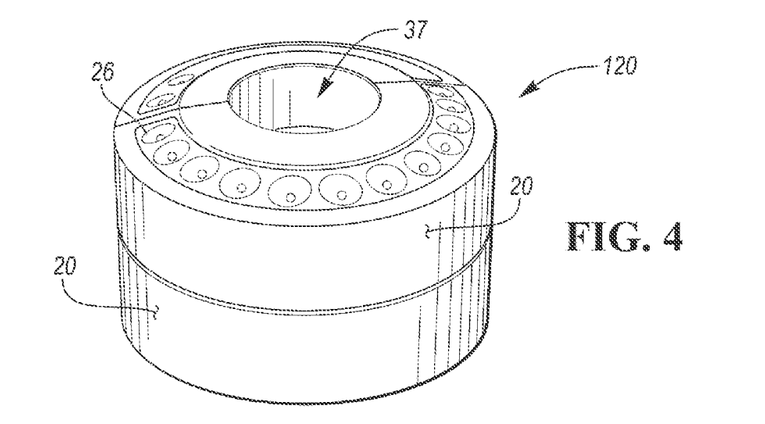
FIG. 4 is a schematic perspective view illustration of an alternative embodiment of the spring-loaded LED-based lighting device shown in FIG. 2.

Referring to FIG. 4, the optional dual clamp-on supplemental lighting devices 120 shown in FIG. 1 may be effectively formed using two of the supplemental lighting devices 20 arranged back-to-back, i.e., with non-light-emitting surfaces of the supplemental lighting devices 20 adjacent to each other. The use of such a supplemental lighting device 120 enables direction of incident red light in multiple directions within the canopy of the flowering plant 12, including upward and downward directions, and possibly including sideways or radial directions when the lighting device 120 is equipped with side-mounted LEDs 26 as shown in the example configuration depicted of FIG. 4.

Figure 5:
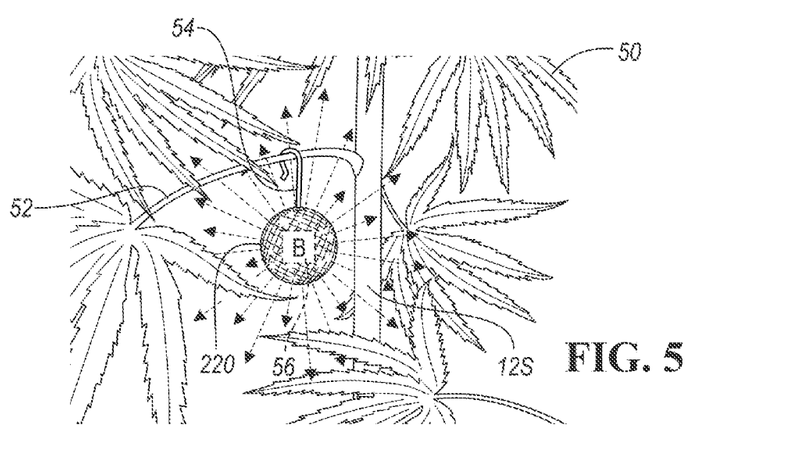
FIG. 5 is a schematic illustration of a flowering plant having a removably-attachable spherical LED-based light device.

An alternative embodiment for multi-directional lighting includes a supplemental lighting device 220 as shown in FIG. 5. As noted above with reference to the supplemental lighting devices 20 and 120, attachment to the stalk 12S may not be ideal in all situations given the potential weight-based implications of such an attachment option. For instance, the diameter of the stalk 12S is typically largest proximate the surface 14S of the soil 14 in FIG. 1 and gradually decreases as one moves upward through the canopy. The supplemental lighting device 220 is thus suited for targeted placement within the canopy to supplement lighting of the side lights 35, particularly on a stem 52 terminating in a leaf 50.

In another optional configuration, the supplemental lighting device 220 may be a spherical arrangement of LEDs 26 analogous to a miniature mirror ball, albeit one that emits light rather than reflects it. The supplemental lighting device 220 is easily attachable to and detachable from the stem 52 or other relatively thin radial protrusion of the stalk 12S. For instance, a hook 54 may be used to removably connect the lighting device 220 to the stem 52 such that the supplemental lighting device 220 hangs gently from the stem 52. The supplemental lighting device 220, given its intended use as a discrete lighting source configured to output red spectrum light as described above in all directions, should be sufficiently lightweight so as not to unduly bend the stem 52 to which it is attached. Ideally, the supplemental lighting device 220 will have its own internal power supply (B) 56, such as a low-voltage battery, although the supplemental lighting device 220 may be powered via a wiring harness (not shown) in other embodiments. The supplemental lighting devices 220 may come in different sizes for use in different portions of the canopy of the flowering plant 12, and possibly with various numbers of LEDs 26 to provide a desired intensity, brightness, or color. The depiction in FIG. 5 is therefore representative of the present teachings and non-limiting.

Figure 6:
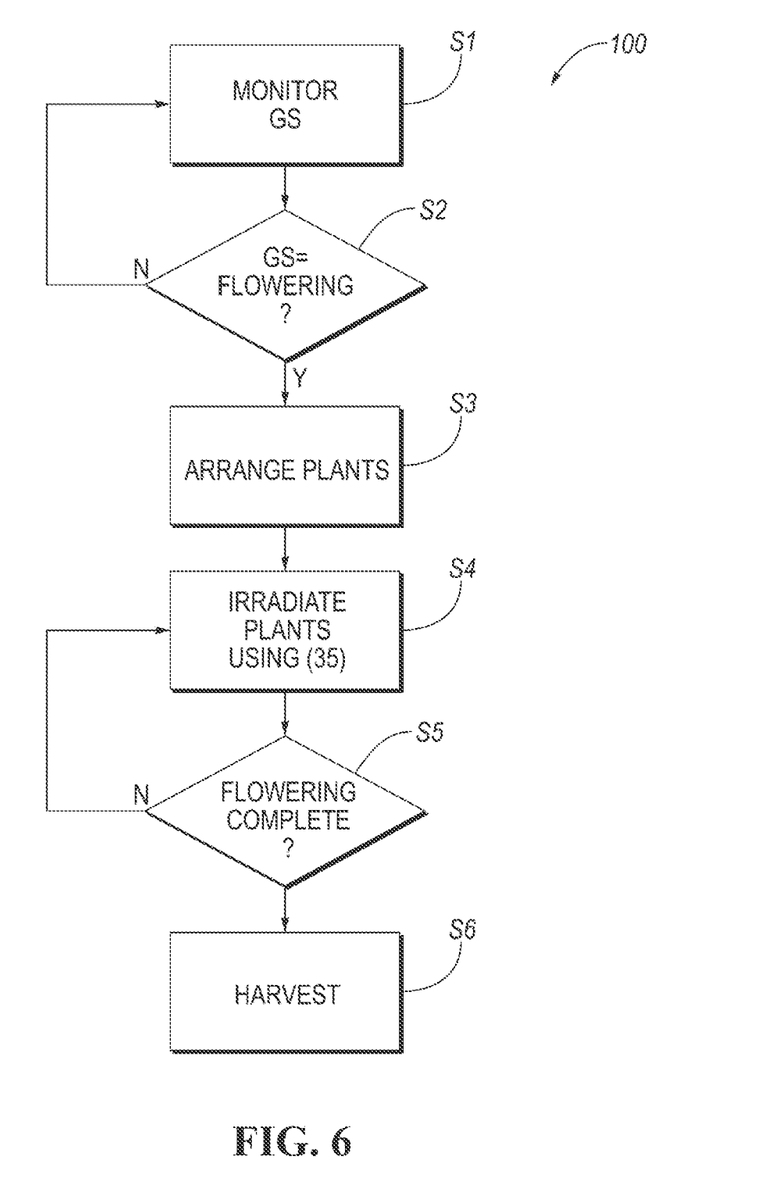
FIG. 6 is a flow chart describing an example method for increasing the floral yield of a flowering plant using one or more of the disclosed LED-based light devices.

Referring to FIG. 6, an example method 100 of increasing the floral yield of a flowering plant such as the flowering plant 12 of FIG. 1 begins with step S1. At step S1, the growth stage (GS) of the flowering plant 10 is carefully monitored over time. In a healthy flowering plant 12 of the type shown in FIG. 1, the seedling stage generally lasts anywhere from 3 weeks to 6 weeks. The vegetative stage follows, with the flowering plant 10 growing rapidly during the vegetative stage. After about 4-6 weeks of growth in the vegetative stage, the flowering plant 12 will enter the flowering stage during which the flowering plant 12 begins to develop floral blooms 19. The actual amount of time a given flowering plant 12 spends in a given lifecycle stage will vary with the plant variety and lighting conditions, and therefore the time ranges noted in step S1 are merely illustrative.

Step S2 includes determining if the present growth stage (GS) of the flowering plant 12 is the flowering stage. Steps S1 and S2 are repeated until the onset of the flowering stage, at which point the method 100 proceeds to step S3.

At step S3, the method 100 includes positioning the flowering plants 12 with respect to the side lights 35 of FIG. 1, or vice versa. For example, step S3 may include arranging the side lights 35 and the vertical racks 18 adjacent to the flowering plants 12 such that the flowering plants 12 are flanked by the side lights 35. Step S3 may optionally include clamping the lighting device 20 and/or 120 directly to the stalk 12S and/or using pressing legs 40 of the lighting device 20 into the soil. Alternatively or concurrently, step S3 may include attaching the lighting devices 220 of FIG. 5 directly to the stems 52. The method 100 proceeds to step S4 after the side lights 35 and possibly the optional lighting devices 20, 120, and/or 220 are positioned on the flowering plants 12 and/or within their respective canopies.

Step S4 entails irradiating the sides of the flowering plants 12 with red spectrum light using the side lights 35, and possibly also with substantially identical red spectrum light that is directed upward, sideways, and/or downward toward the flowering plants 12 using the optional lighting devices 20, 120, and/or 220. The method 100 proceeds to step S5 as step S4 is ongoing.

At step S5, the method 100 includes determining if the flowering stage is complete. Signs of completion of the flowering stage will vary with the variety of the flowering plant 12 being cultivated. In the example of cannabis cultivation, the flowering stage may be considered complete when new floral blooms 13 no longer appear and/or when the pistils on the floral blooms 13 have darkened and begun to curl. The method 100 then proceeds to step S6 when the flowering stage is complete.

Step S6 includes detaching or removing any lighting devices 20, 120, and/or 220 from the flowering plant 12. Thereafter, the flowering plants 12 may be moved away from the side lights 35 or vice versa to facilitate harvesting of the floral blooms 13. If the flowering plants 12 are cannabis plants, the floral blooms 13 are consumable buds, and therefore such floral blooms 13 may be subsequently dried, cured, and processed for consumption. For floral plants yielding fruit, the floral blooms 13 may be left in place on the flowering plants 12 and allowed to continue to develop into fruit, which is then harvested at the appropriate time.

While the best modes for carrying out the present disclosure have been described in detail, those familiar with the art to which this invention relates will recognize various alternative designs and embodiments within the scope of the appended claims.

The invention claimed is:

1. A method for increasing a floral yield of a flowering plant having a total height, the method comprising:
    positioning the flowering plant between side lights, such that the flowering plant is flanked by the side lights;
    commencing, at an onset of a flowering stage of the flowering plant, irradiating of the flowering plant along an entirety of the total height, via the side lights, with light in a predetermined red spectrum range of the electromagnetic spectrum for a duration of the flowering stage, such that at least 95 percent of the light has a wavelength of between 580 nm and 780 nm; and
    discontinuing the irradiating upon completion of the flowering stage.

2. The method of claim 1, wherein positioning the flowering plant between the side lights includes positioning the flowering plant between first and second sets of equally-spaced side lights on respective first and second sides of the flowering plant.

3. The method of claim 2, further comprising:
    attaching one or more supplemental lighting devices to the flowering plant within an interior or under-canopy region of the flowering plant; and
    irradiating the interior or under-canopy region with the light in the predetermined red spectrum range for the duration of the flowering stage using the one or more supplemental lighting devices.

4. The method of claim 3, wherein attaching the one or more supplemental lighting devices to the flowering plant includes clamping at least one an annular clamshell-shaped lighting device directly to a stalk of the flowering plant.

5. The method of claim 4, wherein the flowering plant is rooted in soil, the method further comprising:
    supporting the at least one an annular clamshell-shaped lighting device using a plurality of legs, each respective one of which extends between and at least partially into the annular clamshell-shaped lighting device and the soil.

6. The method of claim 4, wherein the annular clamshell-shaped lighting device has spring-loaded clamps biased by a spring force, and wherein clamping the annular clamshell-shaped lighting device directly to the stalk of the flowering plant occurs solely via the spring force of each of the spring-loaded clamps, such that the stalk is fully circumscribed or surrounded by the annular clamshell-shaped lighting device.

7. The method of claim 6, wherein the annular clamshell-shaped lighting device includes first and second annular clamshell-shaped lighting devices arranged back-to-back such that the light is directed upward and downward into the interior or under-canopy region of the flowering plant.

8. The method of claim 1, wherein the light has a color between 1500 degrees Kelvin and 2700 degrees Kelvin.

9. The method of claim 1, wherein the predetermined range of the electromagnetic spectrum is 585 nm to 740 nm.

10. The method of claim 8, wherein the predetermined range of the electromagnetic spectrum is 600 nm to 700 nm.

11. The method of claim 1, wherein the flowering plant is a cannabis plant.

12. A method for increasing a floral yield of a flowering plant having a total height, the method comprising:
    positioning the flowering plant between parallel first and second sets of equally-spaced elongated side lights, such that the flowering plant is flanked by the side lights, and such that a first respective elongated side light of each of the parallel first and second sets of equally-spaced elongated side lights is positioned proximate a top of the flowering plant, a second respective elongated side light of each of the first and second sets of equally-spaced elongated side lights is positioned proximate a bottom of the flowering plant, and at least a third respective elongated side light of each of the parallel first and second sets of equally-spaced elongated side lights are positioned proximate a middle of the flowering plant;
    attaching at least one supplemental lighting device to an interior or under-canopy region of the flowering plant;
    commencing at an onset of a flowering stage of the flowering plant, irradiating lateral sides of the flowering plant along an entirety of the total height, via the parallel first and second sets of equally-spaced elongated side lights, and irradiating the interior or under-canopy region of the flowering plant via the at least one supplemental lighting device, with light in a predetermined red spectrum range of the electromagnetic spectrum for a duration of the flowering stage, such that at least 95 percent of the light has a wavelength in the predetermined red spectrum range of 580 nm to 780 nm; and
    discontinuing the irradiating upon completion of the flowering stage.

13. The method of claim 12, wherein attaching the at least one supplemental lighting device to the flowering plant includes clamping an annular clamshell-shaped lighting device directly to a stalk of the flowering plant.

14. The method of claim 13, wherein the annular clamshell-shaped lighting device has spring-loaded clamps each biased by a respective spring force, and wherein clamping the annular clamshell-shaped lighting device directly to the stalk of the flowering plant is achieved via the respective spring force of each of the spring-loaded clamps, such that the stalk is fully circumscribed or surrounded by the lighting device.

15. The method of claim 12, wherein the light has a color of between 1500 degrees Kelvin and 2700 degrees Kelvin.

16. The method of claim 12, wherein the predetermined red spectrum range of the electromagnetic spectrum is 585 nm to 740 nm.

17. The method of claim 16, wherein the predetermined red spectrum range of the electromagnetic spectrum is 600 nm to 700 nm.

18. The method of claim 12, wherein the flowering plant is a cannabis plant.

* * * * *